United States Patent
McKeown et al.

[11] Patent Number: 5,942,612
[45] Date of Patent: Aug. 24, 1999

[54] SUBSTITUTED PHTHALOCYANINE LIQUID CRYSTAL COMPOUNDS

[75] Inventors: Neil Bruce McKeown; Guy James Clarkson; Paul Humberstone, all of Manchester, United Kingdom

[73] Assignee: Secretary of State for Defence in her Britannic Majesty's Government of the U.K. of Gt. Britain and N. Ireland Defence Evaluation & Research Agency, United Kingdom

[21] Appl. No.: 08/860,048

[22] PCT Filed: Dec. 21, 1995

[86] PCT No.: PCT/GB95/02996

§ 371 Date: Jun. 20, 1997

§ 102(e) Date: Jun. 20, 1997

[87] PCT Pub. No.: WO96/19480

PCT Pub. Date: Jun. 27, 1996

[30] Foreign Application Priority Data

Dec. 22, 1994 [GB] United Kingdom .................... 9425956

[51] Int. Cl.[6] ......................... C09B 47/04; C07D 487/22
[52] U.S. Cl. ......................... 540/140; 540/139; 540/122; 534/15; 252/299.62; 349/182
[58] Field of Search ..................... 540/139, 140; 534/15; 428/64.7; 252/299.62

[56] References Cited

PUBLICATIONS

Liquid Crystals, vol. 10, No. 3, 1991 London GB, pp. 357–368, Kazuchika Ohta et al. "Discotic liquid crystals oftransition metal complexes".
Chemical Abstracts 118: 158477 & JP 04182485 A2, Sumitomo Chemical Co. 1993.
Chemical Abstracts 118: 70212 & JP 03281386 A2 Toyo Ink MFG Co Ltd. 1993.
Chemical Abstracts 115: 219574 & Liq Cryst (1991), 10(3), 357–68.
Chemical Abstracts 112: 138800 & Kok Akad Nank SSSR (1989), 306(6) 1387–90.
Chemical Abstracts 110: 172956 J Macromol Sci Chem (1988), A25 (10–11) 1227–54.
Chemical Abstracts 109: 139304 & JP 63087282 A2 BASF, 1987.
Chemical Abstracts 106: 102771 & Makromol Chem (1986), 187(11) 2535–44.

Primary Examiner—Mukund J. Shah
Assistant Examiner—Pavanaram K. Sripada
Attorney, Agent, or Firm—Nixon & Vanderhye

[57] ABSTRACT

Phthalocyanines of formula (I) are described wherein M is a metal atom, metal compound or is 2H; one H being bonded to each of the two nitrogen atoms depicted as being bonded to M (positions 29 and 31 shown); $R_1$–$R_{25}$ may be the same or different and are chosen independently from the following groups: straight or branched chain alkyl containing up to 32 carbon atoms where 1 or more non-adjacent $CH_2$ groups may be replaced by O and/or a double bond; H; F; and at least one of $R_{2,3,9,10,16,17,34,24}$ is chosen from formula (II) wherein Y, X and Z are chosen independently from HO, 'O, —O, OR, H, $C_{1-16}$ branched or straight chain alkyl or alkoxy; X and Z may also be selected from phenyl groups which may be, independently of each other, substituted with one or more $C_{1-5}$ straight or branched chain alkyl groups; R may be $C_{1-16}$ branched or straight chain alkyl or alkene wherein 1 or more non-adjacent $CH_2$ groups may be replaced by O and may be terminated by an OH group; provided that at least one of Y, X and Z is chosen from HO, 'O, —O, OR. Compounds of the above formulae are useful in a broad range of applications, including electro-optical devices, Langmuir Blodgett films, molecular wires, in optical recording media and uses which exploit their redox properties.

13 Claims, 3 Drawing Sheets

MEM = OCH2OCH2CH2OCH3

→ A, B → Pcs 11, 16 and 21

Separation by Chromatography from Pc 6 and by-products

Pc 11 —C→ Pc 12

Pc 12 —D→ Pc 13

Pc 12 —E→ Pc 4

Pc 12 —F→ Pc 15

Pc 16 —C→ Pc 17

Pc 17 —D→ Pc 18

Pc 17 —E→ Pc 19

Pc 17 —F→ Pc 20

Pc 21 —C→ Pc 22

Pc 22 —D→ Pc 23

Pc 22 —E→ Pc 24

Pc 22 —F→ Pc 25

SUBSTITUTED PHTHALOCYANINE LIQUID CRYSTAL COMPOUNDS

This application is a 371 of PCT/GB95/02996 filed Dec. 21, 1995.

This invention relates to novel substituted phthalocyanines and to certain uses thereof.

Phtalocyanine has the following formula:

The nomenclature for the numbering of the Benzo portion is also included in the above depiction. Generally substituents in the $R_{2,3,9,10,16,17,23,24}$ positions are referred to as peripheral groups and substituents in the $R_{1,4,8,11,15,18,22,25}$ positions are referred to as non-peripheral groups.

Often, phthalocyanine is abbreviated to Pc.

It is known that some phthalocyanine compounds exhibit liquid crystalline behaviour.

The majority of known liquid crystalline compounds have a generally rod-shaped molecular structure and are often characterised by nematic and/or smectic mesophases. There are, however, a number of known compounds which are characterised by a generally disc-like molecular structure. These compounds are termed discotic compounds, which can be characterised by discotic nematic or columnar mesophase(s).

Discotic compounds can be based on a number of "cores", e.g. benzene, truxene, metallophthalocyanine, phthalocyanines and triphenylene.

Guillon et al Mol. Cryst. Liq. Cryst.; 1985, vol. 130, pp223–229, discuss columnar mesophases from metallated and metal free derivatives of phthalocyanine in which the phthalocyanine is substituted on the benzene rings with various groups all of which are attached to the phthalocyanine core via a $CH_2$ unit.

Piechocki and Simon, New Journal of Chemistry, vol. 9, no 3, 1985, pp159–166, report the synthesis of octa-substituted phthalocyanine derivatives forming discotic mesophases. The side chains are linked to the phthalocyanine core via a $CH_2$ unit.

Most liquid crystal compounds are known as thermotropic liquid crystal compounds. Thermotropic liquid crystals exist in dependence of the temperature in certain temperature intervals. In some cases when different substances are mixed together with a solvent the mixture can exhibit different phases not only as the temperature is changed, but also as the concentration of the solute is changed. When the liquid crystal phase is dependent on the concentration of one component in another it is called a lyotropic liquid crystal. The easiest way to make a lyotropic liquid crystal mixture is to start with a molecule that possesses end groups with different properties. For example one end could show an affinity for water and the other end tends to exclude water. Molecules which possess both a hydrophilic group and a part which is a hydrophobic group can display characteristics of both classes, therefore they are called amphiphilic molecules.

Lyotropic liquid crystals have numerous potential applications including detergents, the recovery of oil from porous rocks and in the food industry for example as food emulsifiers. There may also be medical applications for lyotropic liquid crystal systems. For example, amphiphilic materials could help to make drugs more soluble in the blood.

For a review of phthalocyanine thermotropics, see Simon and Bassoul in Phthalocyanines, Properties and Applications, Ed., C.C. Leznoff and A.B.P. Lever, V.C.H. Publishers 1992, p227.

Some phthalocyanines also absorb radiation in the far-red to near infra-red regions of the electromagnetic spectrum. Compounds which absorb strongly at wavelengths of laser light can in principle be exploited as guest dyes dissolved in liquid crystalline host materials in a laser addressed system.

Materials have been proposed for laser addressed applications in which laser beams are used to scan across the surface of the material or leave a written impression thereon. For various reasons, many of these materials have consisted of organic materials which are at least partially transparent in the visible region. The technique relies upon localised absorption of laser energy which causes localised heating and in turn alters the optical properties of the otherwise transparent material in the region of contact with the laser beam. Thus as the beam traverses the material a written impression of its path is left behind. One of the most important of these applications is in laser addressed optical storage devices, and in laser addressed projection displays in which light is directed through a cell containing the material and is projected onto a screen. Such devices have been described by Khan Appl. Phys. Lett. Vol. 22, p111, 1973; and by Harold and Steele in Proceedings of Euro display 84, pages 29–31, September 1984, Paris, France, in which the material in the device was a smectic liquid crystal material. Devices which use a liquid crystal material as the optical storage medium are an important class of such devices. The use of semiconductor lasers, especially $Ga_xAl_{1-x}As$ lasers where x is from 0 to 1, and is preferably 1, has proven popular in the above applications because they can provide laser energy at a range of wavelengths in the near infra-red which cannot be seen and thus cannot interfere with the visual display, and yet can provide a useful source of well-defined, intense heat energy. Gallium arsenide lasers provide laser light at wavelengths of about 850 nm, and are useful for the above applications. With increasing Al content (x<1), the laser wavelength may be reduced down to about 750 nm.

One of the main problems associated with the use of the above materials is that it has proved difficult to provide materials which are transparent in the visible region and yet are strong absorbers in either the UV or IR region, preferably in the near-IR region. The use of dyes within these materials can provide strong absorption at certain wavelengths, but few dyes are transparent in the visible region and many are insoluble in the type of materials used for laser addressed applications. EP-A-0155780 discloses a group of metal and metal-free phthalocyanines which have been used as infra-red absorbing dyes for a number of applications. These phthalocyanines contain from 5 to 16 peripheral organic substituent groups that are linked to the phthalocyanine through sulphur, selenium, tellurium or nitrogen atoms. However, very few of the groups disclosed absorb infra-red radiation strongly at or near the wavelength of a gallium arsenide laser (850 nm). This problem also applies to a further group of infra-red absorbing phthalocyanines disclosed in EP-A-0134518. This further group consists of naphthalocyanines which are peripherally substituted with alkyl groups and centrally substituted with a metal atom or a chloride, bromide or oxide thereof. Materials Science II/1–2, 1976 pp 39–45 discloses the synthesis of octamethoxyphthalocyanines but these are insoluble in organic solvents and as such are unsuitable for acting as dyes in liquid crystalline solvents for laser addressed systems.

UK Patent GB 2,229,190 B relates to certain novel substituted phthalocyanines, methods for their preparation and to certain uses thereof. For example the compounds described in GB 2,229,190 B are suitable for use in optical recording media, Kuder in J. of Imaging Science. vol. 32, (1988), pp51–56 discusses how phthalocyanine dyes may be used in laser addressed optical recording media; in particular it sets out how active layers may be deposited.

A number of phthalocyanine (Pc) derivatives have been proposed as potential photodynamic therapeutic (PDT) agents. The combination of a sensitizer and electromagnetic radiation for the treatment of cancer is commonly known as photodynamic therapy. In the photodynamic therapy of cancer, dye compounds are administered to a tumour-bearing subject. These dye substances may be taken up, to a certain extent, by the tumour. Upon selective irradiation with an appropriate light source the tumour tissue is destroyed via the dye mediated photogeneration of species such as singlet oxygen or other cytotoxic species such as free radicals, for example hydroxy or superoxide. Most biological studies on Pc compounds related to PDT have been conducted with water soluble sulfonated metallophthalocyanines as described by I. Rosenthal, *Photochem. Photobiol.* 53(6), 859–870, 1991. Methods for synthesizing these compounds often results in mixtures of compounds containing a variety of isomers and/or different degrees of sulfonation.

UK Patent Application 9317881.2 describes substituted metallophthalocyanines and phthalocyanines as PDT agents.

Patent WO 93/09124 describes the use of water soluble salt or acid forms of transition metal phthalocyanines for use in photodynamic therapy. In this patent application, phthalocyanines containing second or third row transition metals with a $d^6$ low-spin electronic configuration are disclosed. The compounds exemplified in patent application WO 93/09124 contain Ru.

Phthalocyanine derivatives have also been used in Langmuir Blodgett films as described in UK Patent 2,229,190 B.

Liquid Crystals, vol. 10, n° 3, 1991, 357–368, EP-A-0252360 and CAS: vol. 118(16), n° 158477a discuss, inter alia peripherally substituted phthalocyanines.

The redox behaviour of phthalocyanines is also of interest. Some uses which exploit the redox properties of phthalocyanines include electrocatalysis, photocatalysis, photovoltaics, electric conduction, photoconductivity and electrochromism. These uses (amongst others) of phthalocyanines are discussed by A.B.P. Lever in Chemtech, 17, pp506–510, 1987.

It is desirable to be able to exert control over the redox properties of phthalocyanine type compounds. Milaeva et al in Doklady Akademic Nauk, SSSR 306, pp1387–90, 1989 have studied dodecachloro-tetra (3,5-di-tert-butyl-4-hydroxy phenyl) phthalocyanine and its redox properties.

According to this invention there is provided phthalocyaniine (Pc) compounds of general Formula I:

Formula I wherein M is a metal atom. metal compound or is 2H: one H being bonded to each of the two nitrogen atoms depicted as being bonded to M (positions 29 and 31) shown):

$R_1$–$R_{25}$ may be the same or different and are chosen independently from the following groups:

stright or branched chain alkyl containing up to 32 carbon atoms where 1 or more non-adjacent $CH_2$ groups may be replaced by 0 and/or a double bond;

H;F;

and at least one of $R_{2,3,9,10,16,17,23,24}$ is chosen from Formula II:

Formula II wherein Y, X and Z are chosen independently from HO, 'O, ⁻O, OR, H, $C_{1-6}$ branched or straight chain alkyl or alkoxy;

X and Z may also be selected from phenyl groups which may be, independently of each other, substituted with one or more $C_{1-5}$ straight or branched chain alkyl groups;

R may be $C_{1-6}$ branched or straight chain alkyl or alkene wherein 1 or more non-adjacent $CH_2$ groups may be replaced by 0 and may be terminated by an OH group, provided that at least one of Y, X and Z is chosen from HO, 'O, ⁻O, OR.

Preferably:

Y is chosen from HO, 'O, ⁻O;

X and Z are chosen independently of each other from H, $C_{1-2}$ branched or straight chain alkyl or alkoxy;

Even more preferably Y possesses one of HO, 'O, ⁻O;

Even more preferably X and Z are both chosen from tertiary butyl, isopropyl, amyl, hydrogen or methyl;

Preferably if Formula II is present on $R_2$, then it is not simultaneously present on $R_3$ and vice versa; and in addition, if Formula II is present on $R_2$ then $R_3$ and $R_1$ are independently chosen from H or F or if Formula II is present on $R_3$ then $R_4$ and $R_2$ are independently chosen from H or F;

Preferably if Formula II is present on $R_9$ then it is not simultaneously present on $R_{10}$ and vice versa; and in addition, if Formula II is present on $R_9$ then $R_8$ and $R_{10}$ are independently chosen from H or F or if Formula II is present on $R_{10}$ then $R_9$ and $R_{11}$ are independently chosen from H or F, Preferably if Formula II is present on $R_{16}$ then it is not simultaneously present on $R_{17}$ and vice versa: and in addition, if Formula II is present on $R_{16}$ then $R_{15}$ and $R_{17}$ are independently chosen from H or F or if Formula II is present on $R_{17}$ then $R_{16}$ and $R_{18}$ are independently chosen from H or F;

Preferably if Formula II is present on $R_{23}$ then it is not simultaneously present on $R_{24}$ and vice versa: and in addition, if Formula II is present on $R_{23}$ then $R_{22}$ and $R_{24}$ are independently chosen from H or F or if Formula II is present on $R_{24}$ then $R_{23}$ and $R_{25}$ are independently chosen from H or F.

The metal atom may be present for example as the metal with an oxidation state of +2 or it may be present with other ligands (or anions) attached to it. These ligands (or anions) may serve the purpose of altering the hydrophobicity of the molecule as a whole. Examples of suitable anions include chloride, bromide or oxide. Examples of suitable metals include Ni, Pb, V, Pd, Co, Nb, Al, Sn, Zn, Cu, Mg, Ca, In, Ga, Fe, Eu, Lu and Ge. Preferably when M is a metal or metal compound then the metal is, or the metal compound contains Cu, Zn, Pb, V, Co, Eu, Lu. Examples of suitable metal compounds include VO.

For compounds described by the current invention the phenoxy group may exist in one of three states, for example as illustrated below:

phenoxy      phenoxy anion      phenoxy radical Radicals described by Formula I may form dimers, or other aggregation effects may occur.

According to a further aspect of this invention phenoxy substituents may combine for example with each other or with the Pc macrocycle to produce an oxidised form, for example:

these quinoid type forms may be produced from the compounds described by Formula I.

The compounds described by the current invention are useful for a broad range of applications.

Many of the compounds described by Formula I show liquid crystalline behaviour and are thus usefully employed in liquid crystal devices. The compounds of Formula I may also be included in a mixture, where the mixture comprises at least two compounds. Typical mixtures include mixtures consisting of compounds of Formula I, and also mixtures comprising at least one compound of Formula I and at least one compound not of Formula I. Donor/acceptor mixtures, and mixtures having lower melting points than melting points of individual compounds, are desirable for obtaining room temperature liquid crystal phases in discotic liquid crystal materials and for control of phase sequence and transition temperatures.

A further aspect of the invention includes use of the compounds of Formula I, and use of mixtures including Formula I, in a liquid crystal device. Typically such devices include linear and non-linear electrical, optical and electro-optical devices, magneto-optical devices, and devices providing responses to stimuli such as temperature changes and total or partial pressure changes.

Many of the compounds described by the present invention may exhibit lyotropic behaviour and may therefore be useful as detergents, recovering oil from porous rocks, in the food industry, providing they are sufficiently non-toxic, for example as emulsifiers. The may also have useful applications in the medical field as detailed earlier.

Polyethylene oxides can complex alkali metal ions, for example Li and have been used as polyelectrolytes in solid state battery applications, see Charadame in 'Macromolecules'. ed. Benoit and Rempp, Pergamon press, New York. 1982, p226. The compounds of the invention may also be useful as polyelectrolytes, they are able to stabilise charge, therefore there exist a number of applications within battery technology.

The compounds of the present invention are suitable for use in optical recording media. Typically the phthalocyanine will absorb in the near-infrared. In order to make an optical recording media using a near-infrared absorber, the near-infrared absorber may be coated or vacuum-deposited onto a transparent substrate. European patent application EP 0 337 209 A2 describes the processes by which the above optical-recording media may be made. Further the materials described in EP 0 337 209 A2 are useful in near-infrared absorption filters and liquid crystal display devices, as are the compounds described by the current invention. As described in EP 0 337 209 A2, display materials can be made by mixing a near-infrared absorber of formula I with liquid crystal materials such as nematic liquid crystals, smectic liquid crystals and cholesteric liquid crystals. The compounds of the current invention may be incorporated into liquid crystal panels wherein the near-infrared absorber is incorporated with the liquid crystal and laser beam is used to write an image. Mixtures of phthalocyanines of the current invention may be mixed with liquid crystal materials in order to be used in guest-host systems. GB 2,229,190 B describes the use of phthalocyanines incorporated into liquid crystal materials and their subsequent use in electro-optical devices.

The materials of the current invention may also be incorporated in Langmuir-Blodgett (LB) films. LB films incorporating phthalocyanines of the current invention may be laid down by conventional and well known techniques, see R.H. Tredgold in 'Order in Thin Organic Films', Cambridge University Press, p74, 1994 and references therein. Generally an LB film is prepared by depositing a monolayer of a surface-active material onto a water surface; this may be done using well established techniques. The molecules of the surface active material alien in the monolayer, the hydrophilic ends remaining in the water, and the hydrophobic end projecting out of the surface. By other known techniques this monolayer may be transferred essentially intact onto the surface of a solid substrate and further monolayers deposited on the layer on the substrate to form a film, i.e. an LB film.

It may be advantageous to polymerise certain of the compounds described by the current invention. Polymerised phthalocyanines may be used in, for example, LB films. There are numerous ways by which the phthalocyanine compound may be polymerised. Polymerisation may be effected via one or more of the positions $R_1-R_{25}$, as described in formula I of the current invention or via the central metal atom or metal compound, or polymerisation may be realised by a combination of the above methods. An example of a suitable phthalocyanine substituent which may be used to effect polymerisation is an unsaturated substituent such as an alkene group.

Main chain or side chain liquid crystal polymers may also be made using the compounds of the present invention, or metal-metal linked liquid crystal polymers.

LB films including compounds of the current invention may be used as optical or thermally addressable storage media.

The compounds of the current invention may also be used as molecular wires, see R.J.M. Nolte et al. Angew. Chem. Int. Ed. Eng., vol. 33, part 21. page 2173, 1994.

It is known that some phthalocyanines are excellent generators of third order non-linear optical effects and thus show promise for use in photonic devices including all-optical switches and computers, see Bredas, Adant, Tackx Persoons and Pierce, Chem. Rev., 94, p243, 1994. The materials of the present invention may show such effects and be used in such devices.

The compounds of the present invention allow for electronic interaction of substituents with the phthalocyanine ring. The redox properties of the phthalocyanines described by the current invention may be easily modified by the introduction of phenolic substituents as described. The compounds described by the current invention are therefore useful in the following:

electrocatalysis, photocatalysis, photovoltaics, electric conduction, photoconductivity and electrochromism and other applications which exploit redox properties.

It is thought that the compounds of the present invention may exhibit suitable redox properties because the phenolic substituents are able to lie in a substantially co-planar orientation in relation to the rest of the phthalocyanine ring. This allows for a degree of orbital overlap of the phenolic ring with the phthalocyanine macrocycle which means that the compounds of the current invention may, exhibit significant electronic coupling with the phthalocyanine ring. Previous studies (including the earlier cited Milaeva et al) have failed to demonstrate significant electronic coupling of the phenolic substituents with the phthalocyanine ring.

The invention will now be described, by way of example only, with reference to the following diagrams.

Figure 1:
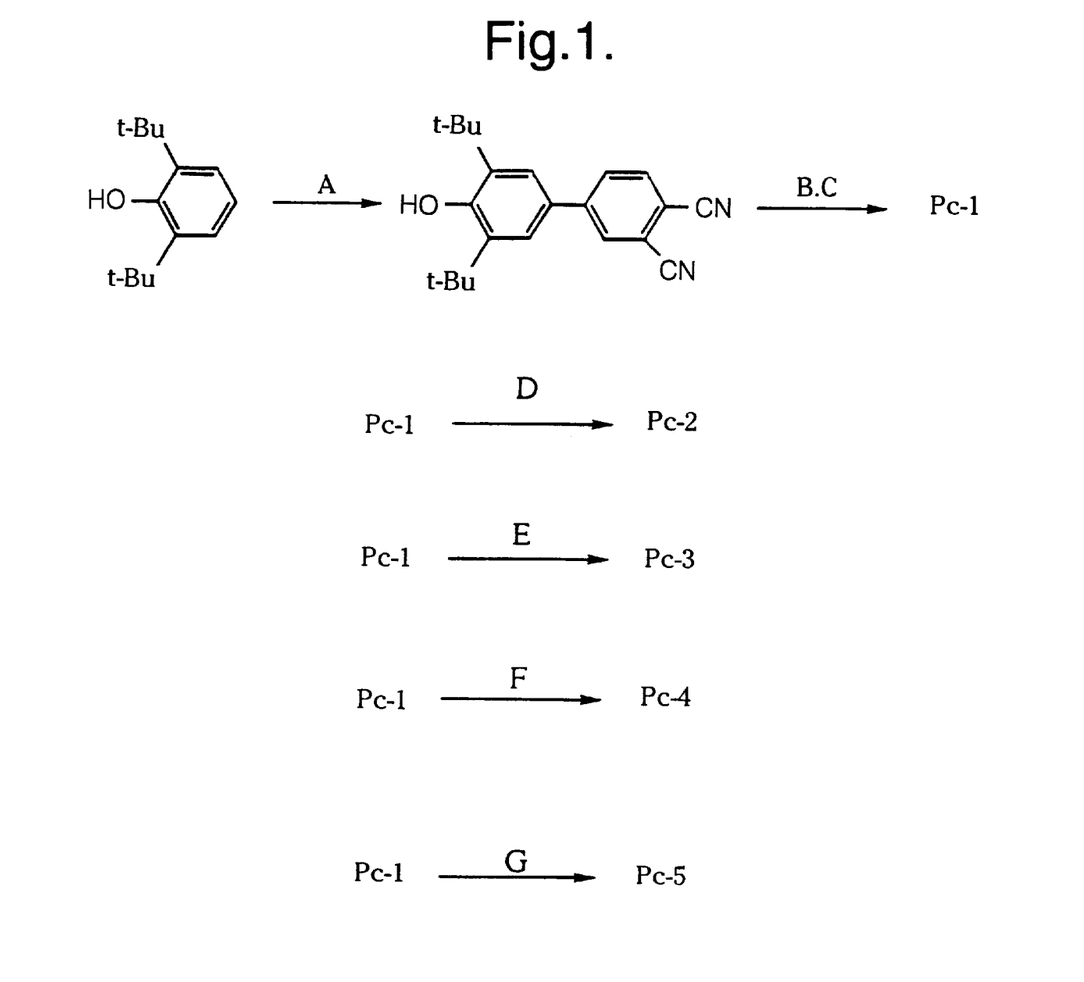
FIGS. 1–3 show synthetic schemes for the preparation of compounds highlighted in Series 1–3.

Reagents used in the synthetic route of FIG. 1 are

A: 4-nitrophthalonitrile, DMF, anhydrous K2CO$_3$, rt, 2 days

B: LiOC$_5$H$_{11}$—C$_5$H$_{11}$OH, 135° C., 2 h

C: AcOH, 0.5 h, rt

D: Tetrabutylammonium hydroxide, toluene rt

E: PbO$_2$, toluene, 1 min, rt

F: aerated solvent (O$_2$), TBAH, 5 days

G: C$_{12}$H$_{25}$Br, anhydrous K$_2$CO$_3$, butanone, 100° C.

where:

DMF=dimethylformamide rt=room temperature

4-Nitrophthalonitrile=

AcOH=acetic acid

Figure 2:
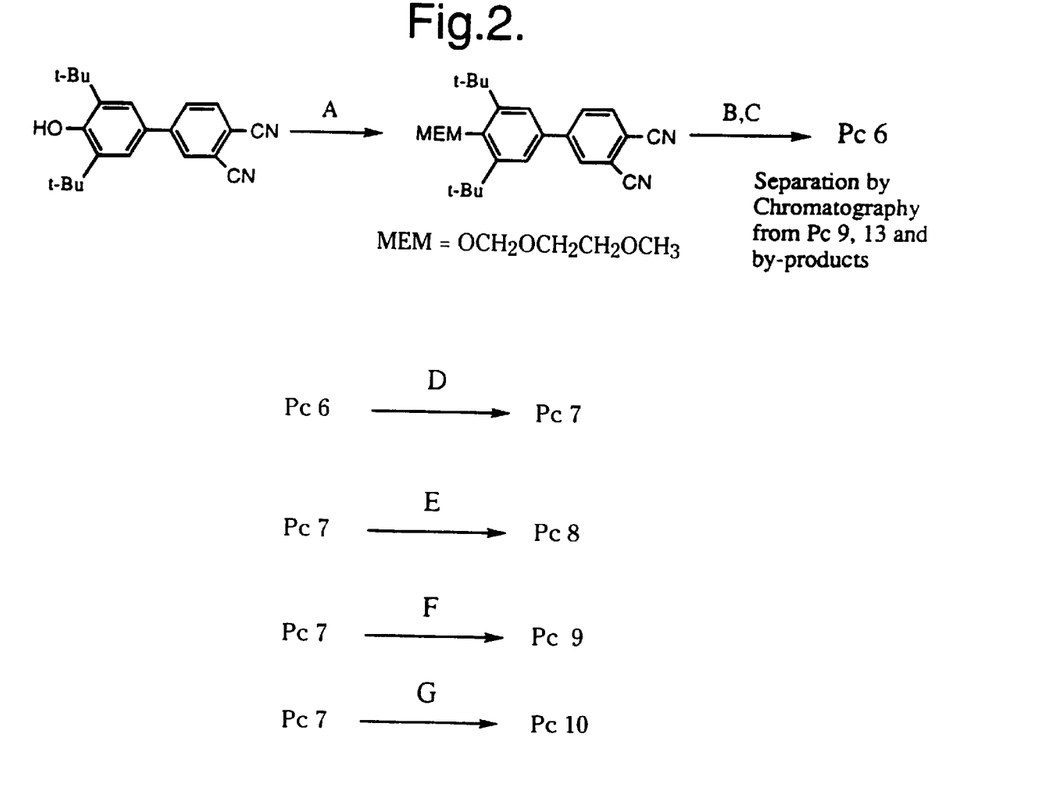

Reagents used in the synthetic route of FIG. 2 are:

A: MEM-Cl, THF, NaH, rt, 24 h

B: 4,5-dihexadecylphthalonitrile (9:1 molar excess), LiOC$_5$H$_{11}$—C$_5$H$_{11}$OH, 135° C., 2 h C: AcOH, 0.5 h, rt D: Pyridinium tosylate, pentanol, 135° C., 4 h E: Tetrabutylammonium hydroxide, toluene rt F: PbO$_2$, toluene, 1 h, rt G: aerated solvent, TBAH, 50° C., 5 days THF=tetrahydrofuran MEM-Cl=CH$_3$OCH$_2$CH$_2$OCH$_2$Cl

NaH=sodium hydride rt=room temperature

ACOH=acetic acid

TBAH=tetrabutylammonium hydroxide

4,5-dihexadecylphthalonitrile= which was made according to the method described by Ohta et al in the New Journal of Chemistry, 1988, 12, 751 and is represented below:

-continued

CuCN/DMF ↓

Figure 3:
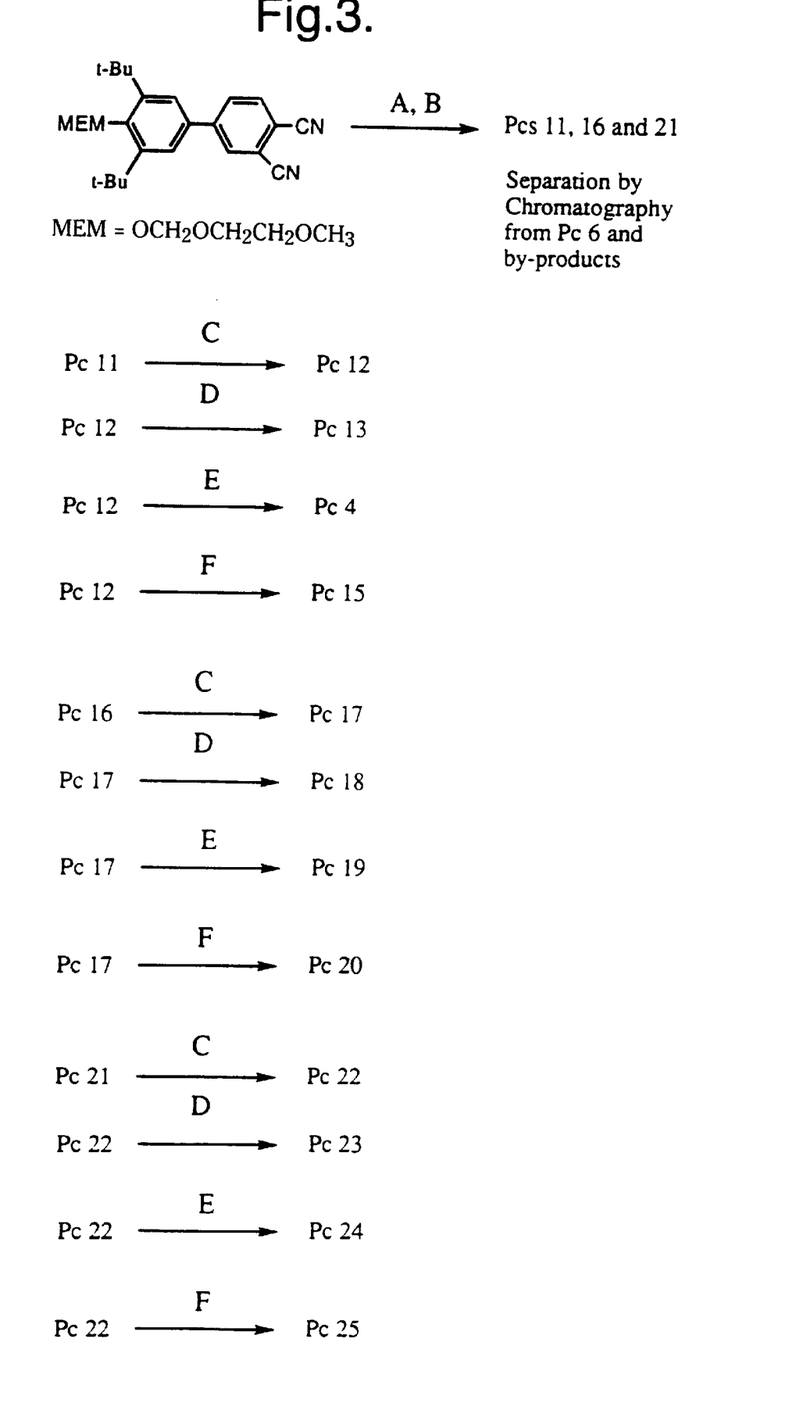

Reagents used in the synthetic route of FIG. 3 are:

A: 4,5-dihexadecylphthalonitrile (equimolarity), LiOC$_5$H$_{11}$—C$_5$H$_{11}$OH, 135° C., 2 h B: AcOH, 0.5 h, rt C: Pyridinium tosylate, pentanol, 135° C., 4 h D: Tetrabutylammonium hydroxide, toluene rt E: PbO$_2$, toluene, 1 min, rt F: aerated solvent. TBAH, 5 days An example of the use of a compound of Formula I in a liquid crystal material and device embodying the present invention will now be described with reference to FIG. 4.

Figure 4:
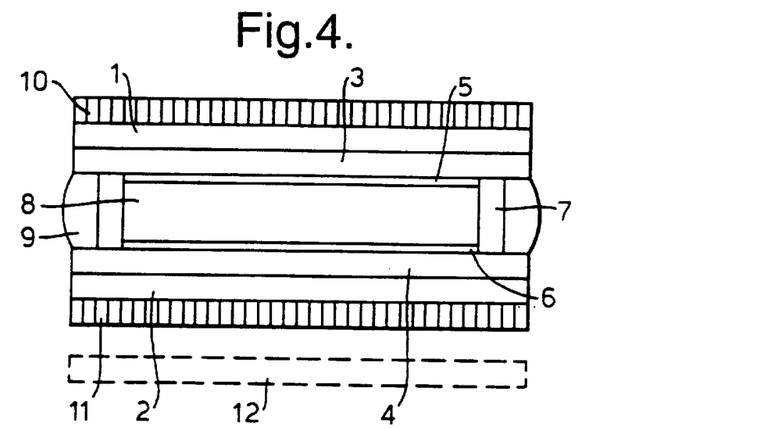
FIG. 4 illustrates a liquid crystal device.

The liquid crystal device consists of two transparent plates, 1 and 2, in this case made from glass. These plates are coated on their internal face with transparent conducting electrodes 3 and 4. An alignment layer 5, 6 is introduced onto the internal faces of the cell so that a planar orientation of the molecules making up the liquid crystalline material will be approximately parallel or at a small angle to the glass plates 1 and 2. For some types of display the plane of the molecules is approximately perpendicular to that of the glass plates, and at each glass plate the alignment directions are orthogonal. The electrodes 3, 4 may be formed into row and column electrodes so that the intersections between each column and row form an x, y matrix of addressable elements or pixels. A spacer 7 e.g. of polymethyl methacrylate separates the glass plates 1 and 2 to a suitable distance e.g. 2 microns. Liquid crystal material 8 is introduced between glass plates 1, 2 by filling the space in between them. The spacer 7 is sealed with an adhesive 9 in a vacuum using an existing technique. Polarisers 10, 11 are arranged in front of and behind the cell. For some devices, only one or even no polarisers are required.

The device may operate in a transmissive or reflective mode. In the former, light passing through the device, e.g. from a tungsten bulb, is selectively transmitted or blocked to form the desired display. In the reflective mode a mirror (12) is placed behind the second polariser 11 to reflect ambient light back through the cell and two polarisers. By making the mirror partly reflecting the device may be operated both in a transmissive and reflective mode.

The alignment layers 5, 6 have two functions one to align contacting liquid crystal molecules in a preferred direction and the other to give a tilt to these molecules—a so called surface tilt—of a few degrees typically around 4° or 5°. The alignment layers 5, 6 may be formed by placing a few drops of the polyimide onto the cell wall and spinning the wall until a uniform thickness is obtained. The polyimide is then cured by heating to a predetermined temperature for a predetermined time followed by unidirectional rubbing with a roller coated with a nylon cloth.

In another example a layer of liquid crystal material is exposed to a gas to provide a gas sensor.

The following compounds are example compounds that have been synthesised for the present invention.

Series A:

1. R = $^1$R = HO— absorption max = 715 nm

2. R = $^1$R = ⁻O— absorption max = 790 nm

3. R = HO—  $^1$R = ⁻O— absorption max = 771 nm 4. two of the substituents are in the oxidised quinoid form:-

5. R = $^1$R = C$_{12}$H$_{25}$O— Dho 105–290° C.

Series B

6. R = $C_{16}H_{33}$-   $^1$R = MEM-[2,6-di-t-Bu-4-Me-phenyl]

MEM = $CH_3OCH_2CH_2OCH_2O$—

7. R = $C_{16}H_{33}$-   $^1$R = HO-[2,6-di-t-Bu-4-Me-phenyl]

8. R = $C_{16}H_{33}$-   $^1$R = $^-$O-[2,6-di-t-Bu-4-Me-phenyl]

9. R = $C_{16}H_{33}$-   $^1$R = $^-$O-[2,6-di-t-Bu-4-Me-phenyl]

10. R = $C_{16}H_{33}$-   $^1$R = O=[2,6-di-t-Bu-4-methylene-cyclohexadienyl]

Series C

11. R = $C_{16}H_{33}$-   $^1$R = MEM-[2,6-di-t-Bu-4-Me-phenyl]

MEM = $CH_3OCH_2CH_2OCH_2O$—

12. R = $C_{16}H_{33}$-   $^1$R = HO-[2,6-di-t-Bu-4-Me-phenyl]

13. R = $C_{16}H_{33}$-   $^1$R = $^-$O-[2,6-di-t-Bu-4-Me-phenyl]

14. R = $C_{16}H_{33}$-   $^1$R = $^-$O-[2,6-di-t-Bu-4-Me-phenyl]

15. R = $C_{16}H_{33}$-   $^1$R = O=[2,6-di-t-Bu-4-methylene-cyclohexadienyl]

-continued

Series D

16. R = C$_{16}$H$_{33}$-

21. R = C$_{16}$H$_{33}$-

17. R = C$_{16}$H$_{33}$-

22. R = C$_{16}$H$_{33}$-

18. R = C$_{16}$H$_{33}$-

23. R = C$_{16}$H$_{33}$-

19. R = C$_{16}$H$_{33}$-

24. R = C$_{16}$H$_{33}$-

20. R = C$_{16}$H$_{33}$-

25. R = C$_{16}$H$_{33}$-

1 Preparation of Phthalonitrile Precursors

Preparation of 4-(3,5-di-tert-butyl-4-hydroxyphenyl)phthalonitrile

To a stirred solution of 4-nitrophthalonitrile (8 g, 0.05 mol) was added 2,6 di-tert-butylphenol (11.44 g, 0.06 mol), potassium carbonate (9 g, 0.07 mol) and DMF (50 ml), producing a deep red colour. The reaction mixture was stirred under a nitrogen atmosphere for 72 h. Water (300 ml) was added and the mixture extracted with ethyl acetate (3×100 ml), the organic layer was further washed with water (3×75 ml) and dried over $MgSO_4$. Evaporation of the solvent under reduced pressure yielded the crude product. Recrystallisation from ethanol yielded the pure product 4-(3,5-di-tert-butyl-4-hydroxyphenyl)phthlonitrile (1) as colourless, prismatic crystals (18.70 g, 81.70%), m.p. 209–210° C.; IR (KBr) 3416 (OH), 2231 (CN) cm$^{-1}$; (Found C, 79.55%; H, 7.50%; N, 8.20%. $C_{22}H_{24}N_2O$ requires C, 79.47%; H, 7.28%; N, 8.43%.); MS (EI) m/e 332 (M$^+$); $\delta_H$ (200 MHz, solvent CDCl$_3$): 1.51 (18H, s), 5.55 (1H, s), 7.39 (2H, s), 7.75–8.00 (3H, m).

Preparation of 4-(3,5-di-tert-butyl-4-(1,3,6-trioxaheptyl)phenyl)phthalonitrile To a stirred solution of 4-(3,5-di-tert-butyl-4-hydroxyphenyl)phathalonitrile (1) (2 g, 6.0 mmole) in dry THF (20 ml), cooled to 0° C., was added sodium hydride (0.28 g, 11.8 mmole) which produced a deep red colour. To this was added MEM chloride (0.82 ml, 7.2 mmole) which was then stirred under a nitrogen atmosphere for 48 h. The reaction mixture was then poured into a 30% ammonia solution (150 ml) and extracted with THF (3×50 ml). The combined THF extracts were then washed with water (2×100 ml) and dried with MgSO$_4$. The THF was removed to give a solid, which was then passed down a silica column firstly eluting with toluene to remove by-products then DCM to remove the impure product. Evaporation of the solvent, followed by recrystallisation from hot ethanol yielded pure 4-(3,5-di-tert-butyl-4-(1,3,6trixaheptyl)phenyl)phathalonitrile as white plates (1.9 g, 75%), m.p. 130–131° C.; IR (evap. film) 2958, 2231(CN), 1598 cm$^{-1}$; (Found C, 74.4%; H, 7.7%; N, 6.5%. $C_{26}H_{32}N_2O_3$ requires C, 74.3%; H, 7.7%; N, 6.7%.); MS (CI) m/e 438 (M$^+$+NH$_4^+$); $\delta_H$ (200 MHz, solvent CDCl$_3$): 1.5 (18H, s), 3.45 (3H, s), 3.65 (2H, t), 4.02 (2H, t), 5.05 (2H, s), 7.45 (2H, s), 7.8–8.0 (3H, m).

Preparation of 4-(3,5-di-tert-butyl-4-(1,3-dioxanonyl)phenyl)phthalonitrile

To a stirred solution of 4-(3,5-di-tert-butyl-4-hydroxphenyl)phthalonitrile (2 g, 6.0 mmole) in dry THF (20 ml), cooled to 0° C., was added sodium hydride (0.28 g, 11.8 mmole) which produced a deep red colour. To this was added bromomethyl octyl ether (2.2 ml, 11.0 mmole) which was then stirred under a nitrogen atmosphere for 48 h. Recrystallisation from hot ethanol yieldedpure 4-(3,5-di-tert-butyl-4-(1,3,-dioxanonyl)phenyl)phthalonitrile as white plates (2.33 g, 82%), m.p. 106–107° C.; IR (evap. film) 2232 (CN); (Found C, 78.57%; H, 8.50%; N, 5.85%. $C_{31}H_{42}N_2O_2$ requires C, 78.42%; H, 8.93%; N, 5.90%.); MS (CI) m/e 492 (M$^+$+NH$_4^+$); $\delta_H$ (200 MHz, solvent CDCl$_3$): 0.80 (3H, t), 1.35 (10H, broad s), 1.50 (18H, s), 1.70 (2H, q), 3.85 (2H, t), 5.00 (2H, s), 7.45 (2H, s), 7.8–8.0 (3H, m).

Preparation of 2,9,16,23-tetra(3,5-di-tert-butyl-4-hydroxyphenyl)phthalonitrile (1)

To a stirred solution of 4-(3,5-di-tert-butyl-4-hydroxyphenyl)phthalonitrile (0.5 g, 1.5 mmol) in dry pentan-1-ol (2 ml) heated to reflux was added an excees of lithium metal (0.05 g, 8 mmol) under a nitrogen atmosphere. The solution turned red immediately. After 1 h the solution turned green. Heating was continued for 4 h after which acetic acid (3 ml) was added, and the mixture was refluxed for 1 h. The pentan-1-ol was removed, under reduced pressure, and the resultant solid was purified by eluting it through a silica column with ethanol (100 ml) then DCM (100 ml). Reprecipitation from ethanol/DCM (9:1) yielded 2,9,16,23-tetra(3,5-di-tert-butyl-4-hydroxyphenzyl)phthalocyanine (1) as a green solid (10 mg, 2%) (Found C, 79.60%; H, 7.50%; N, 9.20%. $C_{88}H_{98}N_8O_4$ requires C, 79.35%; H, 7.42%; N, 8.42%). $\lambda_{max}$(dichloromethane) 715, 683, 652, 620, 344 nm. $\delta_H$ (500 MHz, solvent C$_6$D$_6$, 60° C.): 1.7 (72H, broad s), 5.25 (4H, s), 8.0–8.5 (12H, s), 9.1–10.0 (12H, m). FAB-MS found m/z 1332, $C_{88}H_{98}N_8O_4$ (M$^+$+H$^+$) requires, 1333.

2 Mixed Phthalonitrile Cyclotetramerisation

Preparation of Phthalocyanine Derivatives Containing both Alkyl and MEM Protected Phenolic Substituents Phthalocyanines 6,11,16,21. To a rapidly stirred mixture of 4-(3,5-di-tert-butyl-4-(1,3,6-trioxaheptyl)phenyl)phthalonitrile (0.72 g, 1.71 mmol) and 4,5-bis(hexadecyl)phthalonitrile (1.0 g, 1.73 mmol) in refluxing pentan-1-ol (5 ml), under a nitrogen atmosphere, was added excess lithium metal (0.2 g, 32 mmol). Heating and stirring were continued for 6 h. On cooling, water (30 ml) was added, and the reaction mixture heated to ensure complete Pc demetallisation. Evaporation of the water, under reduced pressure, left a green product mixture. The resultant solid was dissolved in toluene and passed through a silica column, at 50° C., using an eluent composed of an increasing amount of THF relative to toluene. The first fraction (100 mg, 5.8%) (R$_f$=0.9, hot toluene) proved to be identical to a previously prepared sample of 2,3,9,10,16,17,23,24-octa(hexadecyl)phthalocyanine as a blue solid; $\delta_H$ (500 MHz, solvent C$_6$D$_6$, 60° C.): −1.04 (2H), 0.99 (24H, t), 1.3–1.5 (192H, m), 1.80 (16H, m), 2.11 (16H, m), 3.30 (16H, t), 9.62 (8H, s). The second fraction was collected and applied to a fresh silica column (eluent:toluene/heptane, 1:1, 50° C., R$_f$=0.4) and recrystallised from hot toluene to afford 2-(3,5-di-tert-butyl-4-(1,3,6-trioxaheptyl)phenyl)-9,10,16,17,23,24-hexa(hexadecyl)phthalocyanine (6) as a blue solid (140 mg, 8.1%); transition temperatures: 61° C. (K-D$_x$), 170 (D$_x$-D$_{hd}$) and 196 (D$_{hd}$-I); (Found C, 81.54%; H, 11.15%; N, 5.32%. $C_{146}H_{238}N_8O_3$ requires C, 81.43%; H, 11.14%; N, 5.20%). $\lambda_{max}$(toluene) 703, 671, 647, 610, 348 nm. $\delta_H$ (500 MHz, solvent C$_6$D$_6$, 60° C.): −1.3 (2H, broad s), 1.01 (18H, broad t), 1.22–1.7 (144H, broad m), 1.8 (12H, broad m), 1.92 (18H, s), 2.1 (12H, broad m), 3.28 (12H, broad m), 3.38 (3H, s), 3.65 (2H, t), 4.12 (2H, t), 5.37 (2H, s), 8.35 (2H, s), 8.51 (1H, d), 9.15 (1H, s), 9.23 (1H, s), 9.29 (1H, s), 9.33 (1H, s), 9.4 (1H, s), 9.45 (1H, s), 9.62 (1H, s), 10.0 (1H, s). The third fraction was collected and applied to a fresh silica column (eluent:toluene/heptane, 9:1, 50° C., R$_f$=0.25) and recrystallised from dichloromethane into ethanol (1:9) to afford 2,16(17)di(3,5-di-tert-butyl-4-(1,3,6-trioxaheptyl)phenyl)-9,10,23,24-tetra(hexadecyl)phthalocyanine (11) as a mixture of two isomers (60 mg, 3.5%); transition temperatures: 30° C. (K-D$_{hd}$) and 265° C. (D$_{hd}$-I); (Found C, 79.22%; H, 10.21%; N, 5.64%. $C_{132}H_{202}N_8O_6$ requires C, 79.38%; H, 10.20%; N, 5.61%). $\lambda_{max}$(toluene) 720, 695, 681, 651, 623, 387, 345 nm. $\delta_H$ (500 MHz, solvent C$_6$D$_6$, 60° C.): −1.41 (2H, broad s), 1.0 (12H, broad t), 1.2–1.85

(104H, broad m), 1.89 (36H, s), 2.02–2.24 (8H, broad m), 3.1–3.33 (8H, broad m), 3.35 (3H, s), 3.36 (4H, m), 4.12 (4H, m), 5.35 (2H, s), 5.36 (2H, s), 8.30 (2H, s), 8.31 (2H, s), 8.41 (1H, d), 8.45 (1H, d), 9.16 (1H, broad s), 9.28 (1H,broad s), 9.4 (1H, broad s), 9.46 (1H, broad s), 9.49 (1H, broad d), 9.59 (1H, d), 9.89 (1H, s), 9.95 (1H, s). FAB-MS found m/z 1998, $^{13}C_2C_{130}H_{202}N_8O_6$ ($M^+ +H^+$) requires, 1997. The fourth fraction was collected and applied to a fresh silica column (eluent: toluene/THF, 40:1, 20° C., $R_f$=0.2) and recrystallised from ethanol:DCM (9:1) to afford, as a mixture of 3 isomers, 2(3),9(10)-di(3,5-di-tert-butyl-4-(1,3,6-trioxaheptyl)phenyl)- 16,17,23,24-tetra(hexadecyl) phthalocyanine(16) as a blue/green waxy solid (120 mg, 7.0%); transition temperatures: 37° C. (K-$D_{hd}$) and 249° C. ($D_{hd}$-I); (Found C, 79.40%; H, 10.11%; N, 5.63%. $C_{132}H_{202}N_8O_6$ requires C,79.38%; H, 10.20%; N 5.61%). $\lambda_{max}$(DCM) 707, 674, 645, 612, 345 nm. $\delta_H$ (500 MHz, solvent $C_6D_6$, 60° C.): –1.2 (2H, broad s), 1.0 (12H, m), 1.2–1.84 (104H, broad m), 1.89 (9H, s), 1.90 (9H, s), 1.92 (9H, s), 1.95 (9H, s), 2.0–2.2 (8H, broad m), 3.1–3.31 (8H, broad m), 3.35 (3H, s), 3.36 (3H, s), 3.64 (4H, m), 4.11 (4H, m), 5.35 (1H, s), 5.36 (1H, s), 5.37 (1H, s), 5.38 (1H, s), 8.31, 8.32, 8.38, 8.41 (4H, s), 8.52 (2H, m), 9.0–9.48 (4H, broad m), 9.5–9.76 (2H, broad m), 9.84–10.14 (2H, m). FAB-MS found m/z 1998, $^{13}C_2C_{130}H_{202}N_8O_6$ ($M^+ +H^+$) requires, 1997. The fifth fraction was collected and applied to a fresh silica column (eluent: toluene/THF, 20:1, 20° C., $R_f$=0.1) and recrystallised from ethanol/DCM (9:1) to afford, as a mixture of four isomers, 2(3),9(10),16(17)-tri(3,5-di-tert-butyl-4-(1,3,6-trioxaheptyl)phenyl)-23,24-di (hexadecyl)phthalocyanine (21) as a blue/green solid (80 mg, 4.7%); transition temperatures: 45° C. (Glass-$D_{hd}$) and 287° C. ($D_{hd}$-I); (Found C, 77.10%; H, 9.00%; N, 6.20%. $C_{118}H_{166}N_8O_9$ requires C, 77.00%; H, 9.10%; N, 6.10%). $\lambda_{max}$(toluene) 707, 676, 648, 614, 355 nm. $\delta_H$ (500 MHz, solvent $C_6D_6$, 60° C.): –1.4 (2H, broad s), 0.99 (6H, m), 1.28–1.82 (52H, broad m), 1.91 (54H, m), 2.05 (4H,m), 3.1–3.31 (4H, broad m), 3.35 (9H, broad s), 3.64 (6H, broad t), 4.12 (6H, broad t), 5.3–5.42 (6H, broad m), 8.1–8.62 (9H, broad m), 8.84–10.1 (8H, broad m). FAB-MS found m/z 1841, $^{13}CC_{117}H_{166}N_8O_9$ ($M^+ +H^+$) requires, 1841).

3. General Procedure for the Removal of the MEM Group

Preparation of 2-(3,5-di-tert-butyl-4-hydroxyphenyl)-9,10,16,17,23,24-hexa(hexadecyl) phthalocyanine (7)

A mixture of 2-(3,5-di-tert-butyl-4-(1,3,6-trioxaheptyl) phenyl)-9,10,16,17,73,24-hexa(hexadecyl)phthalocyanine (6) (57 mg, 0.03 mmol) and pyridinium p-toluenesulphonate (38 mg, 0.15mmol) in pentan-1-ol (1 ml) was stirred at reflux under a nitrogen atmosphere for 4 h. The pentanol was removed, under reduced pressure, to give a blue solid which was recrystallised from toluene to give 2-(3,5-di-tert-butyl-4-hydroxyphenyl)-9,10,16,17,23,24-hexa(hexadecyl) phthalocyanine (7) as a blue solid (46 mg, 84%), ($R_f$=1.0 hot toluene); transition temperature: 72° C. (K-$D_x$), 96° C. ($D_x$-$D_{hd}$) and 215° C. ($D_{hd}$-I); (Found C, 82.60%; H, 11.25%; N, 5.50%. $C_{142}H_{230}N_8O$ requires C, 82.57%; H, 11.23%; N, 5.43%). $\lambda_{max}$(toluene) 705, 672, 647, 610, 346 nm. $\delta_H$ (500 MHz, solvent $C_6D_6$, 60° C.): –1.28 (2H, broad s), 1.01 (18H, broad t), 1.3–1.9 (156H, broad m), 1.77 (18H, s), 2.14 (12H, broad m), 3.27 (12H, broad m), 5.32 (1H, s), 8.23 (2H, s), 8.51 (1H, d), 9.15 (1H, s), 9.25 (1H, s), 9.26 (1H, s), 9.33 (1H, s), 9.37 (1H, s), 9.41 (1H, s), 9.61 (1H, d), 9.99 (1H, s).

The following Pcs were prepared by the same methodology.

Preparation of 2,16(17)-di(3,5-di-tert-butyl-4-hydroxyphenyl)-9,10,23,24-tetra(hexadecyl) phtlalocyanine (12) (from Pc 11).

Reprecipitated from toluene into ethanol to give a green waxy solid (87%), ($R_f$=0.85: toluene/hexane, 1:2, 20° C.); transition temperature: 17° C. (Glass-$D_{hd}$) and 255° C. ($D_{hd}$-I); (Found C, 81.51%; H, 9.95%; N, 6.13%. $C_{124}H_{186}N_8O_2$ requires C, 81.79%; H, 10.30%; N, 6.16%). $\lambda_{max}$(toluene) 721, 700, 681, 650, 617, 388, 353 nm. $\delta_H$ (500 MHz, solvent $C_6D_6$, 60° C.): –1.6 (2H, broad s), 1.0 (12H, t), 1.2–1.8 (104H, broad m), 1.75 (18H, s), 1.76 (18H, s), 2.09 (8H, m), 3.2 (8H, m), 5.31(1H, s), 5.32 (1H, s), 8.18 (4H, broad s), 8.40 (1H, d), 8.44 (1H, d), 9.08 (1H, broad s), 9.17 (1H, broad s), 9.27 (1H, broad s), 9.33 (1H, broad s), 9.46 (1H, broad s), 9.56 (1H, broad s), 9.84 (1H, broad s), 9.91 (1H, broad s). FAB-MS found m/z 1821, $^{13}CC_{123}H_{186}N_8O_2$($M^+ +H^+$) requires, 1820).

Preparation of 2(3),9(10)-di(3,5-di-tert-buty-4-hydroxyphenyl)-16,17,23,24-tetra(hexadecyl) phtlalocyanine (17) (from Pc 16)

Reprecipitated from toluene into ethanol to give a green waxy solid (79%), ($R_f$=0.48: toluene/hexane, 1:2, 20° C.); transition temperature: 20° C. (Glass-$D_{hd}$) and 195° C. ($D_{hd}$-I); (Found C, 81.99%; H, 10.47%; N, 6.01%. $C_{124}H_{186}N_8O_2$ requires C, 81.79%; H, 10.30%; N, 6.16%). $\lambda_{max}$(toluene) 709, 674, 643, 611, 350 nm. $\delta_H$ (500 MHz, solvent $C_6D_6$, 60° C.): –1.3 (2H, broad s), 1.0 (12H, m), 1.2–1.7 (104H, broad m), 1.75, 1.76, 1.78, 1.81 (36H, s), 2.08 (8H, m), 3.23 (8H, m), 5.32, 5.33, 5.34 (2H, s), 8.19, 8.20, 8.27, 8.30 (4H, s), 8.4–8.6 (2H, broad m), 8.9–9.78 (6H, broad m), 9.86–10.1 (2H, broad m). FAB-MS found m/z 1821, $^{13}CC_{123}H_{186}N_8O_2$ ($M^+ +H^+$) requires, 1820.

Preparation of 2(3),9(10),16(17)-tri(3,5-di-tert-butyl-4-hydroxyphenyl-23,24-di(hexadecyl) phtlalocyanine (22) (from Pc 21)

Reprecipitated from toluene into ethanol to give a green waxy solid (85%); transition temperature: 30° C. (Glass-$D_{hd}$) and 214° C. ($D_{hd}$-I); (Found C, 80.53%; H, 9.45%; N, 7.00%. $C_{106}H_{142}N_8O_3$ requires C, 80.76%; H, 9.08%; N, 7.11%). $\lambda_{max}$(toluene) 710, 679, 653, 616, 348 nn. $\delta_H$ (500 MHz, solvent $C_6D_6$, 60° C.): –1.5 (2H, broad s), 0.99 (6H, t), 1.2–1.65 (52H, broad m), 1.76 (54H, m), 1.8–2.2 (4H, broad m), 3.3 (4H, broad m), 5.24–5.4 (6H, broad m), 8.0–8.6 (9H, broad m), 8.8–10.1 (8H, broad m). FAB-MS found m/e 1576, $^{13}CC_{105}H_{142}N_8O_3$ ($M^+ +H^+$) requires, 1576).

4. General procedure for the Oxidation of Phthalocyanines 1,7,12,17,22 via anions Pc 2,8,13, 18,23

Oxidation of 2-(3,5-di-tert-butyl-4-hydroxyphenyl)-9,10,16,17,23,24-hexa(hexadecyl)phthalocyanine (7) to give (10), To a stirred solution of 2-(3,5-di-tert-butyl-hydroxyphenyl)9,10,16,17,23,24-hexa(hexadecyl) phthalocyanine (7) (35 mg, 0.02 mmol) in toluene (30 ml) heated to 40° C., was added an excess of base tetra-n-butylammonium hydroxide (1 mol $dm^{-3}$ tnBAH-MeOH) which gave an immediate dark blue colour (Pc. The reaction was followed to completion by UV/Vis spectroscopy. The solution was then neutralised by using acetic acid, the organic layer was then washed with water (3×30 ml) and dried over MgSO$_4$. Evaporation of the solvent under reduced pressure yielded a crude product mixture. The resultant mixture was then purified by elution through a silica column with ethanol (50 ml) then DCM (50 ml). Reprecipitation from ethanol/DCM.(9:1) yielded (Pc 10) as a blue solid (23 mg); IR (KBr) 2927, 2851, 1706, 1669, 1611 cm$^{-1}$; $\lambda_{max}$(toluene) 697, 676, 648, 622, 346 nm.

The following oxidised Pcs were prepared by the same methodology, except the solution temperatures were kept at R.T.

Oxidation of 2,9,16,23-tetra(3,5-di-tert-butyl-4-hydroxyphenyl)phthalocyanine (1) to give (4).

Reprecipitated from ethanol/DCM (9:1) to afford (4) as a green solid (5 mg). IR (KBr) 3437, 2923, 2853, 1665, 1643, 1616 cm$^{-1}$; $\lambda_{max}$(toluene) 702, 674 nm.

Oxidation of 2,16(17)-di(3,5-di-tert-butyl-4-hydroxyphenyl)-9,10,23,24-tetra(hexadecyl) phthalocyanine (12) to give (15)

Reprecipitated from ethanol/DCM (9:1) to afford (15) as a green waxy solid (25 mg); IR (KBr) 3642, 3287, 2923, 1664, 1644, 1617 cm$^{-1}$; $\lambda_{max}$(toluene) 690, 619, 341 nm.

Oxidation of 2(3),9(10)-di(3,5-di-tert-butyl-4-hydroxyphenyl)-16,17,23,24-tetra(hexadecyl) phthalocyanine (17) to give (20).

Reprecipitated from ethanol/DCM (9:1) to afford (20) as a green waxy solid (21 mg); IR (KBr) 3642, 2924, 2852, 1663, 1643, 1617, 1502, 1463, 1430 cm$^{-1}$; (Found C, 80.22%; H, 13.17%; N, 6.30%. Unoxidised C$_{124}$H$_{186}$N$_8$O$_2$ (37) requires C, 81.79%; H, 10.30%; N, 6.16%). $\lambda_{max}$ (toluene) 702, 671, 347 nm.

Oxidation of 2(3),9(10),16(17)-tri(3,5-di-tert-butyl-4-hydroxyphenyl)-23,24-di(hexadecyl) phthalocyanine (22) to give (25)

Reprecipitated from ethanol/DCM (9:1) to afford (25) as a green waxy solid (22 mg); IR (KBr) 3437, 2923, 2853, 1665, 1643, 1616 cm$^{-1}$; $\lambda_{max}$(toluene) 697, 675, 342 nm.

is commercially available from Aldrich.

The materials of the current invention may be useful as anti-oxidant materials, for example they may be added to solvents, polymers or foodstuffs such that if sufficient oxidation occurs then a change of colour may result.

For the above data:
D$_{ho}$=discotic hexagonal ordered
N$_c$=nematic columnar
D$_{hd}$=discotic hexagonal disordered
D$_{rd}$=discotic rectangular disordered In another embodiment of the invention, M in formula I may be a non-metal including silicon or compounds of silicon.

We claim:
1. A phthalocyanine of Formula I wherein M is a metal ion, metal compound or is 2H; one H being bonded to each of the two nitrogen atoms depicted as being bonded to M (positions 29 and 31 shown);

R$_1$–R$_{25}$ may be the same or different and are chosen independently from the following groups:

straight or branched chain alkyl containing up to 32 carbon atoms where 1 or more non-adjacent CH$_2$ groups may be replaced by O and/or a double bond;

H; F;

and at least one of R$_{2,3,9,10,16,17,23,24}$ is chosen from Formula II:

wherein Y, X and Z are chosen independently from HO, 'O, $^-$O, OR, H, C$_{1-16}$ branched or straight chain alkyl or alkoxy;

X and Z may also be selected from phenyl groups which may be, independently of each other, substituted with one or more C$_{1-5}$ straight or branched chain alkyl groups;

R may be C$_{1-16}$ branched or straight chain alkyl or alkene wherein 1 or more non-adjacent CH$_2$ groups may be replaced by O and may be terminated by an OH group;

provided that at least one of Y, X and Z is chosen from HO, 'O, $^-$O, OR;

and provided that in the case wherein all of the R$_{2,3,9,10,16,17,23,24}$ positions are chosen from formula II and all of the Y substituents are chosen from OR wherein R is C$_{1-16}$ alkyl then at least one of the X or Z groups is other than H or OR wherein R is C$_{1-16}$ alkyl.

2. A compound according to claim 1 wherein:
Y is chosen from HO, 'O, $^-$O, OR;
X and Z are chosen independently of each other from H, C$_{1-12}$ branched or straight chain alkyl or alkoxy;

if Formula II is present on $R_2$ then it is not simultaneously present on $R_3$ and vice versa; and in addition, if Formula II is present on $R_2$ then $R_3$ and $R_1$ are independently chosen from H or F or if Formula II is present on $R_3$ then $R_4$ and $R_2$ are independently chosen from H or F;

if Formula II is present on $R_9$ then it is not simultaneously present on $R_{10}$ and vice versa; and in addition, if Formula 11 is present on $R_9$ then $R_8$ and $R_{10}$ are independently chosen from H or F or if Formula II is present on $R_{10}$ then $R_9$ and $R_{11}$ are independently chosen from H or F;

if Formula II is present on $R_{16}$ then it is not simultaneously present on $R_{17}$ and vice versa; and in addition, if Formula II is present on $R_{16}$ then $R_{15}$ and $R_{17}$ are independently chosen from H or F or if Formula II is present on $R_{17}$ then $R_{16}$ and $R_{18}$ are independently chosen from H or F;

if Formula II is present on $R_{23}$ then it is not simultaneously present on $R_{24}$ and vice versa; and in addition, if Formula II is present on $R_{23}$ then $R_{22}$ and $R_{24}$ are independently chosen from H or F or if Formula II is present on $R_{24}$ then $R_{23}$ and $R_{25}$ are independently chosen from H or F.

3. A compound according to claim 1 wherein:

Y is chosen from HO, 'O, $^-$O;

X and Z are both chosen from tertiary butyl, isopropyl, amyl, hydrogen or methyl.

4. A compound according to claim 3 wherein M is 2H.

5. A compound according to claim 3 wherein M is a metal ion and is chosen from one of the following metals Ni, Pb, V, Pd, Co, Nb, Al, Sn, Zn, Cu, Mg, Ca, In, Ga, Fe, Eu, Lu and Ge.

6. A compound according to claim 3 wherein M is a metal compound and is an oxide or chloride or bromide of one of the following metals Ni, Pb, V, Pd, Co, Nb, Al, Sn, Zn, Cu, Mg, Ca, In, Ga, Fe, Eu, Lu and Ge.

7. A compound of the formula wherein R and $^1$R are chosen from any of the following:

wherein R" may be selected from $C_{1-16}$ alkyl.

8. A compound of the formula wherein R is $C_{1-20}$ alkyl and $^1$R is chosen from any of the following:

wherein R" may be selected from $C_{1-16}$ alkyl wherein one or more non-adjacent $CH_2$ groups are replaced by oxygen.

9. A compound of the formula wherein R is $C_{1-20}$ alkyl and $^1R$ is chosen from any of the following:

wherein R" may be selected from $C_{1-16}$ alkyl wherein one or more non-adjacent $CH_2$ groups are replaced by oxygen.

10. A compound of the formula wherein R is $C_{1-20}$ alkyl and $^1R$ is chosen from any of the following:

wherein R" may be selected from $C_{1-16}$ alkyl wherein one or more non-adjacent $CH_2$ groups are replaced by oxygen.

11. A compound of the formula wherein R is $C_{1-20}$ alkyl and $^1R$ is chosen from any of the following:

wherein R" may be selected from $C_{1-16}$ alkyl wherein one or more non-adjacent $CH_2$ groups are replaced by oxygen.

12. A mixture of liquid crystal materials including at least one compound of claim 1.

13. A device comprising two spaced cell walls each bearing electrode structures and treated on at least one facing surface with an alignment layer, a layer of a liquid crystal material enclosed between the cell walls, characterised in that it incorporates the mixture as claimed in claim 12.

* * * * *